US010322106B2

(12) United States Patent
Gilbert et al.

(10) Patent No.: US 10,322,106 B2
(45) Date of Patent: Jun. 18, 2019

(54) COMBINATIONS OF AMISULPRIDE AND ANOTHER ANTI-EMETIC FOR TREATING NAUSEA AND VOMITING

(71) Applicant: Acacia Pharma Limited, Cambridgeshire (GB)

(72) Inventors: Julian Clive Gilbert, Cambridgeshire (GB); Robert William Gristwood, Cambridgeshire (GB); Gabriel Fox, Cambridgeshire (GB)

(73) Assignee: Acacia Pharma Limited, Cambridge (GB)

( * ) Notice: Subject to any disclaimer, the term of this patent is extended or adjusted under 35 U.S.C. 154(b) by 0 days.

(21) Appl. No.: 15/565,479

(22) PCT Filed: Apr. 11, 2016

(86) PCT No.: PCT/GB2016/050998
§ 371 (c)(1),
(2) Date: Oct. 10, 2017

(87) PCT Pub. No.: WO2016/162695
PCT Pub. Date: Oct. 13, 2016

(65) Prior Publication Data
US 2018/0071249 A1   Mar. 15, 2018

(30) Foreign Application Priority Data
Apr. 10, 2015  (GB) .................. 1506116.1

(51) Int. Cl.
*A61K 9/00* (2006.01)
*A61K 31/40* (2006.01)
*A61K 45/06* (2006.01)
*A61K 31/439* (2006.01)
*A61K 31/454* (2006.01)
*A61K 31/473* (2006.01)
*A61K 31/496* (2006.01)
*A61K 31/573* (2006.01)
*A61K 31/4178* (2006.01)
*A61K 31/5377* (2006.01)

(52) U.S. Cl.
CPC ............ *A61K 31/40* (2013.01); *A61K 9/0053* (2013.01); *A61K 31/4178* (2013.01); *A61K 31/439* (2013.01); *A61K 31/454* (2013.01); *A61K 31/473* (2013.01); *A61K 31/496* (2013.01); *A61K 31/5377* (2013.01); *A61K 31/573* (2013.01); *A61K 45/06* (2013.01)

(58) Field of Classification Search
None
See application file for complete search history.

(56) References Cited

FOREIGN PATENT DOCUMENTS

WO   WO 2011/110854 A2   9/2011

OTHER PUBLICATIONS

Mattila et al., European Journal of Clinical Pharmacology (1996), 51(2), pp. 161-166.*
Anonymous: "EU Clinical Trials Register EudraCT No. 2013-001635-51", Aug. 19, 2013, https://www.clinicaltrialsregister.eu/ctr-search/trial/2013-001635-51 /DK.
Anonymous: "A trial of APD403 to prevent sickness caused by chemotherapy | Cancer Research UK", Oct. 18, 2013, http://www.cancerresearchuk.org/about-cancer/find-a-clinical-trial/a-trial-of-apd403-to-prevent-sickness-caused-by-chemotherapy.
Anonymous: "Acacia Pharma Announces Positive Results From Phase 2a Nausea & Vomiting Study in Cancer Patients", Oct. 1, 2012, http://www.acaciapharma.com/news/2012/10/acacia-pharma-announces-positive-results-from-phase-2a-nausea-vomiting-study-in-cancer-patients.
Kranke, P. et al. "I.V. APD421 (amisulpride) prevents postoperative nausea and vomiting: a randomized, double-blind, placebo-controlled, multicenter trial", British Journal of Anaesthesia., vol. 111, No. 6, Jul. 19, 2013, pp. 938-945.
Magnani, M. "Amisulpride: Pharmacological and biochemical aspects", Farmacia E Clinica, IT, vol. 33, No. 3, Jan. 1, 1994, pp. 91-97 (Italian, with English Abstract).

* cited by examiner

*Primary Examiner* — Brian J Davis
(74) *Attorney, Agent, or Firm* — Cooley LLP; Heidi A. Erlacher; Chen Chen

(57) ABSTRACT

A kit comprises at least one non-IV injectable unit dose of amisulpride and at least one dose of an acute-phase anti-emetic, for simultaneous, separate or sequential use in the treatment or prevention of chemotherapy- or radiotherapy-induced nausea and/or vomiting in a subject, wherein the subject is receiving or has received a chemotherapy or radiotherapy treatment regimen, and wherein the dosage regimen comprises the administration of the or each acute-phase anti-emetic on day 1, day 1 being the same day that a chemotherapy or radiotherapy is administered, and the administration of the, or at least one of the, non-IV injectable unit doses of amisulpride on day 2. Also provided is a kit comprising at least one non-IV injectable unit dose of amisulpride and at least one unit dose of IV amisulpride. Further provided is a non-IV injectable formulation of amisulpride, for use in the treatment or prevention of delayed-phase chemotherapy- or radiotherapy-induced nausea and/or vomiting in a subject.

16 Claims, No Drawings

COMBINATIONS OF AMISULPRIDE AND ANOTHER ANTI-EMETIC FOR TREATING NAUSEA AND VOMITING

RELATED APPLICATIONS

This application is a U.S. National Phase application, filed under 35 U.S.C. § 371(c), of International Application No. PCT/GB2016/050998, filed on Apr. 11, 2016, which claims the benefit of and priority to United Kingdom Patent Application No. 1506116.1, filed on Apr. 10, 2015. The entire contents of each of these applications are incorporated herein by reference.

FIELD OF THE INVENTION

This invention relates to the use of amisulpride in the therapy of nausea, vomiting and retching associated with cancer chemotherapy and/or radiotherapy.

BACKGROUND OF THE INVENTION

The use of amisulpride as an anti-emetic is described in WO2011/110854, published on 15 Sep. 2011, which claims priority from British Patent Specification, GB 1004020.2, filed on 11 Mar. 2010. Both of these documents are incorporated into this present specification in their entirety.

WO 2011/110855 describes dose ranges of amisulpride which are effective in the treatment of nausea and/or vomiting in man. Preclinical data were provided, which indicated that amisulpride was less effective at higher dosages at inhibiting cisplatin-induced emesis in ferrets. Separately, various formulations were described, including oral and intravenous formulations.

One category of nausea and/or vomiting which can be effectively treated with amisulpride is that associated with chemotherapy and/or radiotherapy. Three types of emesis are associated with the use of emetic chemotherapeutic agents: acute emesis (occurring in the first 24 hours after treatment with the emetic chemotherapeutic agent), delayed emesis (occurring during 24-120 hours after treatment with the emetic chemotherapeutic agent) and anticipatory emesis.

SUMMARY OF THE INVENTION

The present invention is based at least in part on the results of a Phase II clinical trial investigating the combined use of intravenously-administered (IV) and orally-administered amisulpride, for the prevention and treatment of chemotherapy-induced nausea and/or vomiting. According to the clinical trial data as reported herein, it was surprisingly found that a combination of IV and oral amisulpride provides an optimum dosage regimen for treating or preventing both the acute and delayed phases of nausea and/or vomiting. It is believed, based on an understanding of physiology, that these results can be extrapolated to radiotherapy-induced nausea and/or vomiting.

It is believed that the exact nature of the drug in the acute-phase of either CINV or RINV is unimportant, and that any suitable anti-emetic drug could be given in the acute-phase. The key aspect of the present invention is that there is a benefit to combining an acute-phase anti-emetic with a non-IV injectable formulation of amisulpride in the delayed-phase of CINV or RINV. It is intended that the patient will self-administer the amisulpride in the delayed-phase and therefore it should be in the form of a non-IV injectable formulation, preferably an oral formulation.

The results of the clinical trial reported herein also reveal an optimum dosage regimen. This may allow for lower overall amounts of amisulpride to be used over the entire symptomatic period, which offers various benefits to the patient, such as less drug complication, decreased side effects and improved patient compliance. The kits and methods of the invention enable treatment and prophylaxis of both the acute-phase and delayed-phase of nausea and/or vomiting associated with chemotherapy and/or radiotherapy.

A kit comprising at least one non-IV injectable unit dose of amisulpride and at least one dose of an acute-phase anti-emetic, for simultaneous, separate or sequential use in the treatment or prevention of chemotherapy- or radiotherapy-induced nausea and/or vomiting in a subject, wherein the subject is receiving or has received a chemotherapy or radiotherapy treatment regimen, and wherein the dosage regimen comprises the administration of the or each acute-phase anti-emetic on day 1, day 1 being the same day that a chemotherapy or radiotherapy is administered, and the administration of the, or at least one of the, non-IV injectable unit doses of amisulpride on day 2. In one embodiment, the dosage regimen comprises the administration of at least one non-IV injectable unit dose of amisulpride on several days following day 1, for example, on day 2, day 3, and day 4.

According to a second aspect, the present invention provides a kit comprising at least one non-IV injectable unit dose of amisulpride and at least one unit dose of IV amisulpride.

According to a third aspect, the present invention provides a method for the treatment or prevention of chemotherapy- or radiotherapy-induced nausea and/or vomiting, comprising:

step a) administering at least one unit dose of an acute-phase anti-emetic, to a patient in need thereof, wherein the patient is receiving or has received a chemotherapy or radiotherapy; and step b) administering at least one non-IV injectable unit dose of amisulpride to the patient.

In one embodiment, the at least one unit dose of the acute-phase anti-emetic is administered on the same day as the chemotherapy or radiotherapy (i.e. day 1). In one embodiment, the at least one non-IV injectable unit dose of amisulpride is administered on several days following day 1, such as on day 2, day 3, and day 4. In one embodiment, steps a) and b) are repeated each time a chemotherapy or radiotherapy is administered.

According to a fifth aspect, the present invention provides a non-IV injectable formulation of amisulpride, for use in the treatment or prevention of delayed-phase chemotherapy- or radiotherapy-induced nausea and/or vomiting in a subject, wherein the subject is receiving or has received a chemotherapy or radiotherapy treatment regimen on day 1, and wherein the dosage regimen comprises the administration of at least one unit dose of the non-IV injectable amisulpride on day 2.

According to a sixth aspect, the present invention provides a method for the treatment or prevention of delayed-phase chemotherapy- or radiotherapy-induced nausea and/or vomiting, the method comprising administering an effective amount of a non-IV injectable formulation of amisulpride to the patient, wherein at least one the non-IV injectable unit doses of amisulpride is to be administered on day 2, and wherein the patient has received chemotherapy or radiotherapy on day 1.

DESCRIPTION OF THE INVENTION

Amisulpride has a single chiral centre and two enantiomers exist, i.e. (S−)-amisulpride and (R+)-amisulpride. It may be preferred to use the racemate or (S−)-amisulpride, which is substantially free of the (R+)-enantiomer. It has been reported that almost all of the therapeutic activity is to be found in the (S−)-enantiomer, and therefore use of this enantiomer means that it may be possible to reduce the dose by 50% compared to the racemate.

A racemic mixture or racemate of amisulpride means that the amisulpride comprises both the (S−)-amisulpride and the (R+)-enantiomer. For example, the racemic mixture may comprise from 40% to 60% of (S−)-amisulpride and 60% to 40% of the (R+)-enantiomer. In some embodiments, the racemic mixture may comprise about 50% of (S−)-amisulpride and about 50% of the (R+)-enantiomer.

(S−)-amisulpride that is substantially free of the (R+)-enantiomer comprises less than 10%, less than 5%, less than 4%, less than 3%, less than 2%, or less than 1% of (R+)-enantiomer. For example, (S−)-amisulpride that is substantially free of the (R+)-enantiomer comprises less than 2% or less than 1% of (R+)-enantiomer.

Chemotherapy-induced nausea and/or vomiting may be abbreviated herein to CINV and radiotherapy-induced nausea and/or vomiting may be abbreviated herein to RINV.

As used herein, acute-phase CINV is nausea and/or vomiting that occurs within the first 24 hours after a chemotherapy is administered, i.e. after a treatment with the emetic chemotherapeutic agent.

As used herein, delayed-phase CINV is nausea and/or vomiting that occurs from 24 to 120 hours after a chemotherapy is administered, i.e. after a treatment with the emetic chemotherapeutic agent.

As used herein, acute-phase RINV is nausea and/or vomiting that occurs within the first 24 hours after a radiotherapy is administered, i.e. after a radiotherapeutic treatment.

As used herein, delayed-phase RINV is nausea and/or vomiting that occurs from 24 to 120 hours after a radiotherapy is administered, i.e. after a radiotherapeutic treatment.

As used herein, the "acute-phase anti-emetic" is an anti-emetic agent which is suitable for use in the acute-phase of CINV or RINV. The acute-phase anti-emetic is administered via any suitable route, for example IV, oral, rectal or inhaled. It is preferably administered via the intravenous route. The acute-phase anti-emetic agent is typically administered by the medical professional who is administering the chemotherapy or the radiotherapy.

The acute-phase anti-emetic preferably comprises one of more of a 5HT3 antagonist, a corticosteroid and an NK1 inhibitor. A preferred corticosteroid is dexamethasone. Preferred $5HT_3$ antagonists include ondansetron, granisetron and palonosetron, and preferred $NK_1$ antagonists are aprepitant, netupitant or rolapitant. The acute-phase anti-emetic is preferably in an IV formulation, formulated for administration via the intravenous route.

In a preferred embodiment the acute-phase anti-emetic is IV amisulpride or IV amisulpride in combination with ondansetron, or IV amisulpride in combination with ondansetron and dexamethasone. Most preferably, the acute-phase anti-emetic is IV amisulpride.

If the acute phase anti-emetic comprises more than one drug, they are preferably administered within 6, 4, 3, 2 or 1 hour from each other. Most preferably, they are administered at approximately the same time.

As used herein, the term "about" or "approximately", when used together with a numeric value (e.g. 5, 10%, ⅓), refers to a range of numeric values that can be less or more than the number. For example, "about 5" refers to a range of numeric values that are 10%, 5%, 2%, or 1% less or more that 5, e.g. a range of 4.5 to 5.5, or 4.75 to 5.25, or 4.9 to 5.1, or 4.95 to 5.05. In some instances, "about 5" refers to a range of numeric values that are 2% or 1% less or more that 5, e.g. a range of 4.9 to 5.1 or 4.95 to 5.05.

A non-IV injectable amisulpride refers to an amisulpride formulation that is not administered via an intravenous route. A non-IV injectable dosage of amisulpride refers to a dosage of amisulpride formulated for administration via any suitable route other than the intravenous route, i.e. not intended for IV administration.

A non-IV injectable dose of amisulpride in the delayed-phase of CINV or RINV is important as this is in a format that can be self-administered by a patient. There are a number of non-IV injectable formulations known to a person skilled in the art and suitable for use in the invention. In some embodiments, the non-IV injectable formulation is to be administered via the subcutaneous e.g. an injection pen, sublingual, rectal, intranasal, topical (to the skin), buccal or via the pulmonary inhaled route. In some embodiments, the delayed-phase amisulpride is a non-injectable formulation. Preferably, the non-IV injectable formulation for use in the delayed phase of CINV or RINV is an oral formulation, i.e. a formulation that is to be administered via the oral route.

An intravenous amisulpride (or IV amisulpride) refers to an amisulpride formulation for intravenous administration. An intravenous dosage of amisulpride refers to a dosage of an amisulpride formulation for intravenous administration. The acute-phase anti-emetic is preferably administered via an IV route.

As used herein, "therapy" means treatment or prevention. In a preferred embodiment, therapy is treatment and prevention.

The present invention provides a kit comprising at least one unit dose of an acute-phase anti-emetic and at least one non-IV injectable unit dose of amisulpride.

The present invention provides a kit comprising at least one unit dose of an acute-phase anti-emetic and at least one non-IV injectable unit dose of amisulpride.

In one embodiment, the present invention provides a kit comprising at least one non-IV injectable unit dose of amisulpride and at least one intravenous unit dose of amisulpride.

In one embodiment, the kit comprises one, two, three, four, five, or more intravenous unit doses of the acute-phase anti-emetic e.g. amisulpride. In one embodiment, the kit comprises one intravenous unit dose of the acute-phase anti-emetic e.g. amisulpride.

In one embodiment, the kit comprises one, two, three, four, five, or more intravenous unit doses of amisulpride. In one embodiment, the kit comprises one intravenous unit dose of amisulpride.

In one embodiment, the kit comprises one, two, three, four, five, or more non-IV injectable unit doses of amisulpride. In one embodiment, the kit comprises one, two, three, four, or five non-IV injectable unit doses of amisulpride. In one embodiment, the kit comprises one, two, three, or four non-IV injectable unit doses of amisulpride. In one embodiment, the kit comprises one, two, or three non-IV injectable unit doses of amisulpride.

In one embodiment, the kit comprises one intravenous unit dose of amisulpride, and one, two, three, four, five, or more non-IV injectable unit doses of amisulpride. In one embodiment, the kit comprises one intravenous unit dose of amisulpride, and one, two, three, four, or five non-IV injectable unit doses of amisulpride. In one embodiment, the kit comprises one intravenous unit dose of amisulpride, and one, two, three, or four non-IV injectable unit doses of amisulpride. In one embodiment, the kit comprises one intravenous unit dose of amisulpride, and one, two, or three non-IV injectable unit doses of amisulpride.

In one embodiment, the intravenous unit dose of amisulpride comprises 5 to 30 mg, 5 to 25 mg, 5 to 20 mg, 5 to 15 mg, 5 to 12.5 mg, or 5 to 10 mg amisulpride, wherein the amisulpride is in the form of a racemic mixture. In one embodiment, the intravenous unit dose of amisulpride comprises 7.5 to 30 mg, 7.5 to 25 mg, 7.5 to 20 mg, 7.5 to 15 mg, 7.5 to 12.5 mg, or 7.5 to 10 mg amisulpride, wherein the amisulpride is in the form of a racemic mixture. In one embodiment, the intravenous unit dose of amisulpride comprises 10 to 30 mg, 10 to 25 mg, 10 to 20 mg, 10 to 15 mg, 10 to 12.5 mg, or about 10 mg amisulpride, wherein the amisulpride is in the form of a racemic mixture. In one embodiment, the intravenous unit dose of amisulpride comprises about 2.5 mg, about 5 mg, about 7.5 mg, about 10 mg, about 12.5 mg, about 15 mg, about 20 mg, about 25 mg, or about 30 mg amisulpride, wherein the amisulpride is in the form of a racemic mixture. In one embodiment, the intravenous unit dose of amisulpride comprises 10 to 20 mg amisulpride, wherein the amisulpride is in the form of a racemic mixture. In one embodiment, the intravenous unit dose of amisulpride comprises about 10 mg or about 20 mg amisulpride, wherein the amisulpride is in the form of a racemic mixture.

In one embodiment, the intravenous unit dose of amisulpride comprises 2.5 to 15 mg, 2.5 to 12.5 mg, 2.5 to 10 mg, 2.5 to 7.5 mg, 2.5 to 6.25 mg, 2.5 to 5 mg amisulpride, wherein the amisulpride is in the form of (S−)-amisulpride, and substantially free of the (R+)-enantiomer. In one embodiment, the intravenous unit dose of amisulpride comprises 3.75 to 15 mg, 3.75 to 12.5 mg, 3.75 to 10 mg, 3.75 to 7.5 mg, 3.75 to 6.25 mg, 3.75 to 5 mg amisulpride, wherein the amisulpride is in the form of (S−)-amisulpride, and substantially free of the (R+)-enantiomer. In one embodiment, the intravenous unit dose of amisulpride comprises 5 to 15 mg, 5 to 12.5 mg, 5 to 10 mg, 5 to 7.5 mg, 5 to 6.25 mg, or about 5 mg amisulpride, wherein the amisulpride is in the form of (S−)-amisulpride, and substantially free of the (R+)-enantiomer. In one embodiment, the intravenous unit dose of amisulpride comprises 5 to 10 mg amisulpride, wherein the amisulpride is in the form of (S−)-amisulpride, and substantially free of the (R+)-enantiomer. In one embodiment, the intravenous unit dose of amisulpride comprises about 5 mg or about 10 mg amisulpride, wherein the amisulpride is in the form of (S−)-amisulpride, and substantially free of the (R+)-enantiomer.

In one embodiment, the non-IV injectable unit dose of amisulpride comprises 5 to 40 mg, 5 to 35 mg, 5 to 30 mg, 5 to 25 mg, 5 to 20 mg, 5 to 15 mg, 5 to 12.5 mg, or 5 to 10 mg amisulpride, wherein the amisulpride is in the form of a racemic mixture. In one embodiment, the non-IV injectable unit dose of amisulpride comprises 7.5 to 40 mg, 7.5 to 35 mg, 7.5 to 30 mg, 7.5 to 25 mg, 7.5 to 20 mg, 7.5 to 15 mg, 7.5 to 12.5 mg, or 7.5 to 10 mg amisulpride, wherein the amisulpride is in the form of a racemic mixture. In one embodiment, the non-IV injectable unit dose of amisulpride comprises 10 to 40 mg, 10 to 35 mg, 10 to 30 mg, 10 to 25 mg, 10 to 20 mg, 10 to 15 mg, 10 to 12.5 mg, or about 10 mg amisulpride, wherein the amisulpride is in the form of a racemic mixture. In one embodiment, the non-IV injectable unit dose of amisulpride comprises 5 to 20 mg amisulpride, wherein the amisulpride is in the form of a racemic mixture. In one embodiment, the non-IV injectable unit dose of amisulpride comprises 5 to 15 mg amisulpride, wherein the amisulpride is in the form of a racemic mixture. In one embodiment, the non-IV injectable unit dose of amisulpride comprises 7.5 to 12.5 mg amisulpride, wherein the amisulpride is in the form of a racemic mixture. In one embodiment, the non-IV injectable unit dose of amisulpride comprises about 10 mg amisulpride, wherein the amisulpride is in the form of a racemic mixture.

In one embodiment, the non-IV injectable unit dose of amisulpride comprises 2.5 to 20 mg, 2.5 to 17.5 mg, 2.5 to 15 mg, 2.5 to 12.5 mg, 2.5 to 10 mg, 2.5 to 7.5 mg, 2.5 to 6.75 mg, or 2.5 to 5 mg amisulpride, wherein the amisulpride is in the form of (S−)-amisulpride, which is substantially free of the (R+)-enantiomer. In one embodiment, the non-IV injectable unit dose of amisulpride comprises 3.75 to 20 mg, 3.75 to 17.5 mg, 3.75 to 15 mg, 3.75 to 12.5 mg, 3.75 to 10 mg, 3.75 to 7.5 mg, 3.75 to 6.75 mg, or 3.75 to 5 mg amisulpride, wherein the amisulpride is in the form of (S−)-amisulpride, which is substantially free of the (R+)-enantiomer. In one embodiment, the non-IV injectable unit dose of amisulpride comprises 5 to 20 mg, 5 to 17.5 mg, 5 to 15 mg, 5 to 12.5 mg, 5 to 10 mg, 5 to 7.5 mg, 5 to 6.75 mg, or about 5 mg amisulpride, wherein the amisulpride is in the form of (S−)-amisulpride, which is substantially free of the (R+)-enantiomer. In one embodiment, the non-IV injectable unit dose of amisulpride comprises 2.5 to 10 mg amisulpride, wherein the amisulpride is in the form of (S−)-amisulpride, which is substantially free of the (R+)-enantiomer. In one embodiment, the non-IV injectable unit dose of amisulpride comprises 2.5 to 7.5 mg amisulpride, wherein the amisulpride is in the form of (S−)-amisulpride, which is substantially free of the (R+)-enantiomer. In one embodiment, the non-IV injectable unit dose of amisulpride comprises 3.75 to 6.25 mg amisulpride, wherein the amisulpride is in the form of (S−)-amisulpride, which is substantially free of the (R+)-enantiomer. In one embodiment, the non-IV injectable unit dose of amisulpride comprises about 5 mg amisulpride, wherein the amisulpride is in the form of (S−)-amisulpride, which is substantially free of the (R+)-enantiomer.

Any one or more intravenous unit dose of amisulpride described herein can be combined with any one or more non-IV injectable unit doses of amisulpride described herein. In one embodiment, any one intravenous unit dose of amisulpride described herein can be combined with any one or more non-IV injectable unit doses of amisulpride described herein. In one embodiment, the kit of the invention comprises one intravenous unit dose of amisulpride comprising 10 to 20 mg amisulpride, wherein the amisulpride is in the form of a racemic mixture, and one, two, three, four, five, or more non-IV injectable unit doses of amisulpride comprising 5 to 20 mg amisulpride, wherein the amisulpride is in the form of a racemic mixture. In a further embodiment, the kit comprises one, two, or three non-IV injectable unit doses of amisulpride comprising 5 to 20 mg amisulpride, wherein the amisulpride is in the form of a racemic mixture. In a further embodiment, the kit comprises one, two, or three non-IV injectable unit doses of amisulpride comprising 5 to 15 mg amisulpride, wherein the amisulpride is in the form of a racemic mixture. In a further embodiment, the kit comprises one, two, or three non-IV injectable unit doses of amisulpride comprising 7.5 to 12.5 mg amisulpride, wherein the amisulpride is in the form of a racemic mixture. In one embodiment, the kit of the invention comprises one intravenous unit dose of amisulpride comprising about 10 mg or about 20 mg amisulpride, wherein the amisulpride is in the form of a racemic mixture, and one, two, or three non-IV injectable unit doses of amisulpride comprising about 10 mg amisulpride, wherein the amisulpride is in the form of a racemic mixture.

In one embodiment, the kit of the invention comprises one intravenous unit dose of amisulpride comprising 5 to 10 mg amisulpride, wherein the amisulpride is in the form of (S−)-amisulpride, and substantially free of the (R+)-enantiomer, and one, two, three, four, five, or more non-IV injectable unit doses of amisulpride comprising 5 to 20 mg amisulpride, wherein the amisulpride is in the form of a racemic mixture. In a further embodiment, the kit comprises one, two, or three non-IV injectable unit doses of amisulpride comprising 5 to 20 mg amisulpride, wherein the amisulpride is in the form of a racemic mixture. In a further embodiment, the kit comprises one, two, or three non-IV injectable unit doses of amisulpride comprising 5 to 15 mg amisulpride, wherein the amisulpride is in the form of a racemic mixture. In a further embodiment, the kit comprises one, two, or three non-IV injectable unit doses of amisulpride comprising 7.5 to 12.5 mg amisulpride, wherein the amisulpride is in the form of a racemic mixture. In one embodiment, the kit of the invention comprises one intravenous unit dose of amisulpride comprising about 5 mg or about 10 mg amisulpride, wherein the amisulpride is in the form of (S−)-amisulpride, and substantially free of the (R+)-enantiomer, and one, two, or three non-IV injectable unit doses of amisulpride comprising 10 mg amisulpride, wherein the amisulpride is in the form of a racemic mixture.

In one embodiment, the kit of the invention comprises one intravenous unit dose of amisulpride comprising 10 to 20 mg amisulpride, wherein the amisulpride is in the form of a racemic mixture, and one, two, three, four, five, or more non-IV injectable unit doses of amisulpride comprising 2.5 to 10 mg amisulpride, wherein the amisulpride is in the form of (S−)-amisulpride, and substantially free of the (R+)-enantiomer. In a further embodiment, the kit comprises one, two, or three non-IV injectable unit doses of amisulpride comprising 2.5 to 10 mg amisulpride, wherein the amisulpride is in the form of (S−)-amisulpride, and substantially free of the (R+)-enantiomer. In a further embodiment, the kit comprises one, two, or three non-IV injectable unit doses of amisulpride comprising 2.5 to 7.5 mg amisulpride, wherein the amisulpride is in the form of (S−)-amisulpride, and substantially free of the (R+)-enantiomer. In a further embodiment, the kit comprises one, two, or three non-IV injectable unit doses of amisulpride comprising 3.75 to 6.25 mg amisulpride, wherein the amisulpride is in the form of (S−)-amisulpride, and substantially free of the (R+)-enantiomer. In one embodiment, the kit of the invention comprises one intravenous unit dose of amisulpride comprising about 10 mg or about 20 mg amisulpride, wherein the amisulpride is in the form of a racemic mixture, and one, two, or three non-IV injectable unit doses of amisulpride comprising 5 mg amisulpride, wherein the amisulpride is in the form of (S−)-amisulpride, and substantially free of the (R+)-enantiomer.

In one embodiment, the kit of the invention comprises one intravenous unit dose of amisulpride comprising 5 to 10 mg amisulpride, wherein the amisulpride is in the form of (S−)-amisulpride, and substantially free of the (R+)-enantiomer, and one, two, three, four, five, or more non-IV injectable unit doses of amisulpride comprising 2.5 to 10 mg amisulpride, wherein the amisulpride is in the form of (S−)-amisulpride, and substantially free of the (R+)-enantiomer. In a further embodiment, the kit comprises one, two, or three non-IV injectable unit doses of amisulpride comprising 2.5 to 10 mg amisulpride, wherein the amisulpride is in the form of (S−)-amisulpride, and substantially free of the (R+)-enantiomer. In a further embodiment, the kit comprises one, two, or three non-IV injectable unit doses of amisulpride comprising 2.5 to 7.5 mg amisulpride, wherein the amisulpride is in the form of (S−)-amisulpride, and substantially free of the (R+)-enantiomer. In a further embodiment, the kit comprises one, two, or three non-IV injectable unit doses of amisulpride comprising 3.75 to 6.25 mg amisulpride, wherein the amisulpride is in the form of (S−)-amisulpride, and substantially free of the (R+)-enantiomer. In one embodiment, the kit of the invention comprises one intravenous unit dose of amisulpride comprising about 5 mg or about 10 mg amisulpride, wherein the amisulpride is in the form of (S−)-amisulpride, and substantially free of the (R+)-enantiomer, and one, two, or three non-IV injectable unit doses of amisulpride comprising 5 mg amisulpride, wherein the amisulpride is in the form of (S−)-amisulpride, and substantially free of the (R+)-enantiomer.

The present invention provides a method for the treatment or prevention of chemotherapy- or radiotherapy-induced nausea and/or vomiting, comprising:

step a) administering at least one unit dose of an acute-phase anti-emetic, to a patient in need thereof, wherein the patient is receiving or has received a chemotherapy or radiotherapy; and step b) administering at least one non-IV injectable unit dose of amisulpride to the patient.

In one embodiment, the at least one unit dose of an acute-phase anti-emetic is administered on the same day as the chemotherapy or radiotherapy is administered. Alternatively, each unit dose of an acute-phase anti-emetic is administered on the same day as the day on which the chemotherapy or radiotherapy is administered. In one embodiment, the at least one unit dose (e.g., IV unit dose) is administered before (e.g. about 6, 5, 4, 3, 2 or 1 hour before) or at about the same time as the chemotherapy or radiotherapy is administered or up to 4 hours after the chemotherapy or radiotherapy is administered. In one embodiment, the acute-phase anti-emetic is an IV amisulpride. In one embodiment, the IV amisulpride is administered according to IV unit dose described herein.

The various embodiments for the kit described above are also applicable to all aspects of the invention, i.e. the kit, for use, and the method.

In one embodiment, a plurality of non-IV injectable unit doses of amisulpride are administered. On the basis that the chemotherapy or radiotherapy and the acute-phase anti-emetic (e.g., IV amisulpride), if present, are given on day 1, in one embodiment, at least one non-IV injectable unit dose is administered on day 2. In a further embodiment, at least one non-IV injectable unit dose is administered on each of days 2 and 3. In a further embodiment, at least one non-IV injectable unit dose is administered on each of days 2, 3 and 4. Further non-IV injectable unit doses may be administered on further consecutive days, e.g. days 5, 6 and 7.

In one embodiment, the unit doses of amisulpride are administered approximately 24 hours apart on consecutive days, i.e. the unit doses of amisulpride are to be administered at approximately the same time each day. Alternatively, it is possible that the daily dose may be split for multiple administrations.

The present invention provides a non-IV injectable formulation of amisulpride, for use in the treatment or prevention of delayed-phase chemotherapy- or radiotherapy-induced nausea and/or vomiting in a subject, wherein the subject has received a chemotherapy or radiotherapy treatment regimen on day 1, and wherein the dosage regimen comprises the administration of at least one unit dose of the non-IV injectable amisulpride on day 2. In some embodiments, the subject has received an acute-phase anti-emetic (preferably as defined herein) on day 1.

The present invention provides a method for the treatment or prevention of delayed-phase chemotherapy- or radiotherapy-induced nausea and/or vomiting, the method comprising administering an effective amount of a non-IV injectable formulation of amisulpride to the patient, wherein at least one the non-IV injectable unit doses of amisulpride is to be administered on day 2, and wherein the patient has received chemotherapy or radiotherapy on day 1.

In some embodiments, the patient has received an acute-phase anti-emetic (preferably as defined herein) on day 1.

As used herein "a chemotherapy" or "a radiotherapy" means a dose of a chemotherapeutic agent, or a dose of radiotherapy. A dose of a chemotherapeutic agent is typically given as an intravenous infusion over a period of time. A chemotherapy or radiotherapy dose may be part of an overall regimen, wherein multiple doses are administered, for example, every two weeks.

In one embodiment, the chemotherapy or radiotherapy treatment regimen may comprise more than one administration of the chemotherapeutic or radiotherapeutic agent, and accordingly steps a) and b) are repeated each time the chemotherapy or radiotherapy is administered.

A kit or method of the invention is useful in the therapy of chemotherapy-induced nausea and/or vomiting or radiotherapy-induced nausea and/or vomiting. As used herein, the term "nausea and/or vomiting" is preferably "nausea and vomiting", i.e. a kit or method of the invention is efficacious for treating or preventing both symptoms. A kit or method of the invention may be particularly beneficial in treating or preventing nausea indications.

In a preferred embodiment, a kit or method of the invention is useful in the therapy of chemotherapy-induced nausea and/or vomiting.

A kit of the invention may be used in therapy (treatment and/or prevention) of both acute-phase CINV (or RINV) and delayed-phase CINV (or RINV). It is particularly useful in therapy of delayed-phase CINV (or RINV).

A kit of the invention preferably comprises at least one unit dose of amisulpride for intravenous injection which is sterile. It is preferably packaged with instructions specifying how the active agent should be administered.

Preferably, the instructions specify use in the therapeutic indication of chemotherapy-induced nausea and/or vomiting or radiotherapy-induced nausea and/or vomiting.

As used herein, the term "day" means a calendar day, i.e. on a particular date of a month, from midnight to midnight. The dosage regimen and method of the invention is given in terms of an agent being given on day 1, day 2, day 3, day 4 and so on. It is to be understood that these are consecutive days in a particular dosing period. For example, the chemotherapy or radiotherapy is commenced on day 1, and therefore days 2, 3, 4, etc. should be understood to be consecutive days following the commencement of the chemotherapy or radiotherapy.

Preferably, the unit dose of the acute-phase anti-emetic (e.g., amisulpride) is administered on the same day as the chemotherapy or radiotherapy is administered. Alternatively, each unit dose of the acute-phase anti-emetic (e.g., amisulpride) is administered on the same day as the day on which the chemotherapy or radiotherapy is administered. At least one acute-phase anti-emetic unit dose is preferably administered before the chemotherapy or radiotherapy is administered or up to 4 hours afterwards. More preferably, "before" in this context means about 6, 5, 4, 3, 2 or 1 hour before. It may be given at the same time as the chemotherapy or radiotherapy is administered e.g. as an infusion of a chemotherapeutic agent begins. In one embodiment, there is one single IV anti-emetic unit dose (e.g., IV amisulpride) administered, according to the preferred schedule detailed above.

In a preferred embodiment, there is a plurality of non-IV injectable unit doses of amisulpride in a dosage regimen/method of the invention. On the basis that the chemotherapy or radiotherapy and the acute-phase antiemetic (e.g., IV amisulpride) is given on day 1, it is preferred that there is at least one non-IV injectable unit dose administered on day 2. Preferably, there are non-IV injectable unit doses administered on days 2 and 3. More preferably, there are non-IV injectable unit doses administered on days 2, 3 and 4. Further non-IV injectable unit doses may be administered on further consecutive days, e.g. days 5, 6 and 7.

It is preferred that there are approximately 24 hours between doses when the dosing is carried out on consecutive days, i.e. that the agent is to be administered at approximately the same time each day. However, it is possible that the daily dose may be split into multiple doses, for example, a morning and an evening dose.

Most preferably, the first non-IV injectable unit dose of amisulpride is administered as early as practically possible after waking of the patients on day 2, i.e. the day following that on which a chemotherapy or radiotherapy is administered, with subsequent non-IV injectable unit doses administered at intervals of approximately 24 hours thereafter.

It is possible that a non-IV injectable unit dose of amisulpride may be given on the same day that a chemotherapy or radiotherapy is administered.

In a preferred embodiment, there is a plurality of non-IV injectable unit doses of amisulpride in a kit/method of the invention. Preferably, there are 2, 3 or 4 non-IV injectable unit dosages, and most preferably there are 3 unit dosages of the non-IV injectable formulation of amisulpride, to be administered on days 2, 3 and 4.

Preferably, the unit dose of an acute-phase anti-emetic comprises 5 to 30 mg of amisulpride, more preferably 10 to 20 mg, and most preferably about 20 mg or about 10 mg, preferably wherein the amisulpride is in the form of a racemic mixture.

Preferably, the unit dose of an acute-phase anti-emetic comprises 2.5 to 15 mg of amisulpride, more preferably 5 to 10 mg, and most preferably about 5 mg, wherein the amisulpride is in the form of (S−)-amisulpride, and substantially free of the (R+)-enantiomer.

It may be advantageous to use the amisulpride kit of the invention in a method of the invention in combination with other classes of drug which can add additional benefits of efficacy. Preferably, the other class of drug is a different anti-emetic agent (i.e. an anti-emetic that is different from the one in the kit). These include, but are not limited to, steroids, most preferably dexamethasone, $5HT_3$ antagonists including but not limited to ondansetron, granisetron and palonosetron, and $NK_1$ antagonists such as aprepitant, netupitant or rolapitant.

As used herein, a "delayed-phase anti-emetic" is an anti-emetic that is administered in the delayed-phase of CINV or RINV. It may be selected from the anti-emetics listed above. It is preferably in a non-IV injectable formulation.

Typical doses of the different anti-emetic agents listed above will be known to a person skilled in the art. For example, ondansetron is typically in a dose of from 2 to 20 mg, or 2 to 15 mg, or about 10 mg. For granisetron, the dose is typically 1-3 mg. For dexamethasone, a typical dose is from 4-20 mg.

The delayed-phase or the acute-phase anti-emetic (which may be selected from the list of "other classes of drug" mentioned above), may be administered on the same day as the, or at least one of the, non-IV injectable unit doses and/or the IV unit doses of amisulpride. If it is administered with at least one non-IV injectable unit dose (a delayed-phase anti-emetic), it is preferred that it is administered with each of the at least one non-IV injectable unit doses. Preferably, each non-IV injectable unit dose of amisulpride comprises 5 to 40 mg of amisulpride, more preferably 5 to 20 mg, more preferably still 5 to 15 mg and most preferably about 10 mg, preferably wherein the amisulpride is in the form of a racemic mixture.

Preferably, each non-IV injectable unit dose of amisulpride comprises 2.5 to 20 mg of amisulpride, more preferably 2.5 to 10 mg, more preferably still 2.5-7.5 mg and most preferably about 5 mg, wherein the amisulpride is in the form of (S−)-amisulpride, which is substantially free of the (R+)-enantiomer.

Preferably, the non-IV injectable unit dose of amisulpride is given once a day. However, the non-IV injectable unit dose may be split into multiple doses, for example, a morning dose and an evening dose, or multiple doses given at more regular intervals.

For any dosage regimen or method recited herein, the instructions for use accompanying a kit of the invention preferably specify this dosage regimen or method.

An intravenous formulation for use in the invention (e.g. intravenous formulation of amisulpride) may be in the form of a salt, hydrate or solvate. Salts include pharmaceutically acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example, alkali metal salts such as sodium and potassium salts and alkali earth metal salts such as magnesium and calcium salts, and organic amine salts, such as morpholine, piperidine, dimethylamine and diethylamine salts.

An intravenous formulation for use in the invention (e.g. intravenous formulation of amisulpride) may be in the form of a sterile injectable aqueous or non-aqueous (e.g. oleaginous) solution or suspension. The sterile injectable preparation may also be in a sterile injectable solution or suspension in a non-toxic parenterally-acceptable diluent or solvent, for example, a solution in 1,3-butanediol. Among the acceptable vehicles and solvents that may be employed are water, phosphate buffer solution, Ringer's solution and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid may be used in the preparation of the intravenous formulation of the invention. Suspensions may be formulated according to the known art using those suitable dispersing or wetting agents and suspending agents.

Aqueous suspensions contain the active ingredient in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl or n-propyl p-hydroxybenzoate, one or more colouring agents, one or more flavouring agents, and one or more sweetening agents, such as sucrose or saccharin.

Compositions for injection are typically aqueous, and comprise a buffer, e.g. citrate buffer. No other ingredients may be required. The pH of such a composition may be, for example from 4 to 7, e.g. about 5.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are known.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate.

An intravenous unit dose of amisulpride for use in the invention is preferably a single injection containing amisulpride. In a preferred embodiment, this could be in the form of a vial of the active agent(s) along with a syringe and needle or a prefilled syringe/needle combination.

An non-IV injectable unit dose (e.g. of amisulpride) for use in the invention may be in the form of a solid or liquid formulation, and may be formulated for oral administration. The solid formulations may be in the form of a tablet or capsule, a melt tablet, or in the form of a dispersible powder or granules (that may need to be added to water). Liquid formulations may be in the form of an aqueous or oily suspension or in the form of a syrup, and they may be packaged in a vial.

A non-IV injectable formulation of amisulpride may be in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical delivery, transdermal and transmucosal patches, creams, ointments, jellies, solutions or suspensions may be employed. For sub-lingual delivery, fast dissolving tablet formulations may be used, as well as a number of the presentations described above. For oral administration, which is preferred amisulpride may be administered as tablets, capsules or liquids.

In a preferred embodiment, an oral unit dose of amisulpride is in the form of one of more tablets, or one or more capsules. The non-IV injectable unit doses of amisulpride may be provided in a blister pack.

The non-IV injectable formulations may contain any number of pharmaceutically acceptable excipients, such as sweeteners and preservatives.

Suitable intravenous and non-IV injectable formulations of amisulpride which can be used in the kit are described in WO2011/110854.

Where a kit and/or a method of the invention provides for the administration of more than one drug, they can be administered simultaneous, sequentially or separately. It is not necessary that they are packed together (but this is one embodiment of the invention). It is also not necessary that they are administered at the same time. As used herein, "separate" administration means that the drugs are administered as part of the same overall dosage regimen (which could comprise a number of days), but preferably on the same day. As used herein "simultaneously" means that the drugs are to be taken together or formulated as a single composition. As used herein, "sequentially" means that the drugs are administered at about the same time, and preferably within about 1 hour of each other.

The following studies illustrate the invention.

Study 1

This study was designed to find the optimum dose range of IV amisulpride for the kit and method of the invention.

This was an open label, ascending dose, Phase II study to determine the minimum effective dose of intravenous amisulpride in the prevention of cisplatin-induced nausea and vomiting. The number of patients evaluated was 51. Doses of amisulpride (racemic mixture) administered were 2.5, 7.5 and 20 mg. A 20 mg dose of amisulpride was also administered with a standard dose of IV ondansetron.

No emesis (vomiting/retching) was seen in 0/5 patients in the 2.5 mg group, 0/5 patients in the 7.5 mg group, 3/18 patients in the 20 mg group and 19/23 patients in the 20 mg and ondansetron combination group.

No significant nausea was seen in 1/5 patients in the 2.5 mg group, 1/5 patients in the 7.5 mg group, 12/18 patients in the 20 mg group and 19/23 patients in the 20 mg and ondansetron combination group.

Protection from nausea with intravenous amisulpride showed a positive dose-relationship from 2.5 mg to 20 mg. A 20 mg IV dose of amisulpride in combination with a standard IV dose of ondansetron gave excellent protection from acute cisplatin-induced nausea and vomiting, with a complete response rate of 82.6%, significantly more than would be expected with ondansetron alone.

Study 2

A randomised, double blind Phase II clinical study was conducted to characterise the dose-response of oral amisulpride for the prevention of acute and delayed phase nausea and vomiting in male and female patients. The patent population consisted of adult, chemotherapy-naïve cancer patients, receiving a first infusion of either cisplatin chemotherapy at a dose of 70 mg/m$^2$ or greater, or a combination of cyclophosphamide (500-1500 mg/m$^2$) and either epirubicin (60-100 mg/m$^2$) or doxorubicin (40-60 mg/m$^2$) for breast cancer.

All patients received an intravenous injection of 20 mg of amisulpride (racemic mixture) and an intravenous injection of 8-16 mg ondansetron on the day of chemotherapy administration (i.e. day 1). The oral doses of amisulpride (racemic mixture) studied, along with placebo, were 10 mg, 20 mg or 40 mg each administered once per day on days 2-4 after chemotherapy. Specifically one capsule of amisulpride or its matching placebo, were taken as early as practically possible after waking of the patients each morning on days 2, 3 and 4.

The efficacy data are shown in Table 1 below:

| | IV OND + 20 mg AMI (day 1) followed on days 2-4 by oral regimen of: | | | | | | | |
|---|---|---|---|---|---|---|---|---|
| | Placebo | | 10 mg AMI | | P | 20 mg AMI | | 40 mg AMI |
| Number of subjects | 65 | | 59 | | P | 67 | | 64 |
| CR, 24-120 h | 13 | 20% | 27 | 46% | 0.002 | 21 | 31% | 20 | 31% |
| Vomiting, 24-120 h | 41 | 63% | 27 | 46% | 0.040 | 37 | 55% | 37 | 58% |
| Rescue medication use, 24-120 h | 38 | 58% | 26 | 41% | 0.078 | 36 | 54% | 36 | 56% |
| Nausea, 24-120 h | 53 | 82% | 37 | 63% | 0.016 | 46 | 69% | 46 | 72% |
| CR, 0-120 h | 11 | 17% | 21 | 36% | 0.015 | 17 | 25% | 17 | 27% |
| Vomiting, 0-120 h | 48 | 74% | 35 | 59% | 0.064 | 47 | 70% | 42 | 66% |
| Rescue medication use, 0-120 h | 44 | 68% | 32 | 54% | 0.088 | 37 | 55% | 37 | 58% |
| Nausea, 0-120 h | 55 | 85% | 40 | 68% | 0.023 | 48 | 72% | 49 | 77% |
| Patients with acute phase CR | 25 | | 28 | | | 30 | | 36 |
| CR, 24-120 h | 11 | 44% | 21 | 75% | 0.022 | 17 | 57% | 17 | 47% |
| Vomiting, 24-120 h | 11 | 44% | 6 | 21% | 0.072 | 13 | 43% | 17 | 47% |
| Rescue medication use, 24-120 h | 9 | 36% | 4 | 14% | 0.065 | 7 | 23% | 13 | 36% |
| Nausea, 24-120 h | 18 | 72% | 9 | 32% | 0.004 | 14 | 47% | 22 | 61% |

AMI: amisulpride
OND: ondansetron
CR: complete response

The data show that 10 mg oral amisulpride on days 2-4 gives significantly higher delayed-phase complete response than placebo (46% vs. 20%, p=0.002). There is also significantly less emesis, nausea and use of rescue medication.

The complete response rate was superior with 10 mg oral amisulpride, while the 20 mg and 40 mg doses were also efficacious, but not as good as 10 mg, suggesting that 10 mg is the optimum dose.

For acute-phase responders, 10 mg is significantly better than placebo (p=0.04) and as good as the best available three-drug regimen (a 5HT3 antagonist, a corticosteroid and an NK1 inhibitor) in terms of delayed phase response. "Delayed phase response" means complete response (composite endpoint defined as no voting/retching and no use of rescue medication) in the period 24-120 hrs after chemo. There are other benefits of using a kit of the invention compared to three-drug regimen, such as reduced side-effects and better patient compliance.

The results show that the benefits in nausea are especially marked for acute-phase responders (p=0.004 vs. placebo).

The invention claimed is:

1. A kit comprising at least one non-IV injectable unit dose of amisulpride and at least one unit dose of an acute-phase anti-emetic, for use in the treatment or prevention of chemotherapy- or radiotherapy-induced nausea and/or vomiting in a subject, wherein the subject is receiving or has received a chemotherapy or radiotherapy, and wherein the, or each of the at least one acute-phase anti-emetic is for use on the same day as the chemotherapy or radiotherapy, and the at least one non-IV injectable unit dose of amisulpride is for use as a delayed-phase anti-emetic on the day following the chemotherapy or radiotherapy.

2. The kit, for use according to claim 1, wherein the acute-phase anti-emetic comprises amisulpride, ondansetron and/or dexamethasone.

3. The kit, for use according to claim 1, wherein the kit additionally comprises at least one unit dose of another delayed-phase anti-emetic agent for use on the same day as the at least one non-IV injectable unit dose of amisulpride.

4. The kit, for use according to claim 3, wherein the another delayed-phase anti-emetic agent is a $5HT_3$ antagonist, an $NK_1$ antagonists or a steroid.

5. A kit comprising at least one non-IV injectable unit dose of amisulpride and at least one unit dose of IV amisulpride.

6. The kit according to claim 5, comprising a single intravenous unit dose of amisulpride and a plurality of non-IV injectable unit doses of amisulpride.

7. The kit according to claim 5, additionally comprising at least one unit dose of another anti-emetic agent.

8. The kit according to claim 7, wherein the another anti-emetic agent is a $5HT_3$ antagonist, an $NK_1$ antagonists or a steroid.

9. A method for the treatment or prevention of chemotherapy- or radiotherapy-induced nausea and/or vomiting, the method comprising:
    step a) administering at least one unit dose of an acute-phase anti-emetic to a patient in need thereof, wherein the patient is receiving or has received a chemotherapy or radiotherapy; and
    step b) administering an effective amount of at least one non-IV injectable unit dose of amisulpride as a delayed-phase anti-emetic to the patient.

10. The method according to claim 9, wherein the or each of the at least one unit dose of the acute-phase anti-emetic is to be administered on day 1, day 1 being the same day that the chemotherapy or radiotherapy is administered, and wherein the at least one non-IV injectable unit dose of amisulpride is to be administered on day 2.

11. The method according to claim 9, wherein the patient is to be administered at least one unit dose of another delayed-phase anti-emetic on the same day as the at least one non-IV injectable unit dose of amisulpride.

12. The method according to claim 11, wherein the another delayed-phase anti-emetic agent is a $5HT_3$ antagonist, an $NK_1$ antagonist or a steroid.

13. A method for the treatment or prevention of delayed-phase chemotherapy- or radiotherapy-induced nausea and/or vomiting, the method comprising administering an effective amount of a non-IV injectable formulation of amisulpride to a patient in need thereof, wherein at least one unit dose of the non-IV injectable formulation of amisulpride is to be administered as a delayed-phase anti-emetic on day 2, and wherein the patient has received chemotherapy or radiotherapy on day 1.

14. The method according to claim 13, wherein the patient is receiving or has received an acute-phase anti-emetic on day 1.

15. The method according to claim 13, further comprising administering at least one unit dose of another delayed-phase anti-emetic on day 2, on days 2 and 3, or on days 2, 3 and 4.

16. The method according to claim 15, wherein the another delayed-phase anti-emetic is a $5HT_3$ antagonist, an $NK_1$ antagonist or a steroid.

* * * * *